United States Patent
Cham

[11] Patent Number: 5,744,038
[45] Date of Patent: Apr. 28, 1998

[54] SOLVENT EXTRACTION METHODS FOR DELIPIDATING PLASMA

[75] Inventor: Bill Elliot Cham, Sheldon, Australia

[73] Assignee: Aruba International PTY Ltd., Rocklea, Australia

[21] Appl. No.: 592,379

[22] PCT Filed: Jul. 22, 1994

[86] PCT No.: PCT/AU94/00415

§ 371 Date: Jan. 30, 1996

§ 102(e) Date: Jan. 30, 1996

[87] PCT Pub. No.: WO95/03840

PCT Pub. Date: Feb. 9, 1995

[30] Foreign Application Priority Data

Jul. 30, 1993 [AU] Australia ............... PM0287

[51] Int. Cl.⁶ ............... B01D 11/00; A61M 1/36
[52] U.S. Cl. ............... 210/634; 210/643; 210/738; 210/782; 210/790; 210/806; 436/177; 436/178; 530/422; 604/4; 604/5; 604/6
[58] Field of Search ............... 210/634, 643, 210/738, 781, 782, 790, 806, 219, 456; 436/177, 178; 530/422, 424; 604/4, 5, 6; 422/256, 257, 258, 259

[56] References Cited

U.S. PATENT DOCUMENTS

| | | | |
|---|---|---|---|
| 4,235,602 | 11/1980 | Meyer et al. | 210/634 |
| 4,258,010 | 3/1981 | Rozsa et al. | 422/257 |
| 4,645,512 | 2/1987 | Johns | 210/634 |
| 4,668,398 | 5/1987 | Silvis | 210/634 |
| 4,680,320 | 7/1987 | Uku et al. | 210/634 |
| 4,879,037 | 11/1989 | Utzinger | 210/634 |
| 4,895,558 | 1/1990 | Cham | 604/4 |
| 5,112,956 | 5/1992 | Tang et al. | 210/634 |
| 5,393,429 | 2/1995 | Nakayama et al. | 210/634 |

FOREIGN PATENT DOCUMENTS

| | | |
|---|---|---|
| 0 036 283 | 9/1981 | European Pat. Off. |
| 0 267 471 | 5/1988 | European Pat. Off. |
| 55-127104 | 10/1980 | Japan. |
| 5-277303 | 10/1993 | Japan. |
| 1204224 | 1/1986 | U.S.S.R. |

*Primary Examiner*—John Kim
*Attorney, Agent, or Firm*—Panitch Schwarze Jacobs & Nadel, P.C.

[57] ABSTRACT

A separating device for extracting cholesterol from plasma uses a spinner to disperse plasma into an extracting solvent in the form of fine droplets to improve separation efficiency, thereby making it suitable for delipidating blood plasma. Blood plasma is delipidated by providing the plasma to the spinner and dispersing the plasma into the extracting solvent in fine droplets. A de-emulsification step removes residual solvent from the plasma. Blood is removed from an animal and the blood plasma is delipidated. Delipidated plasma is de-emulsified and combined with the animal blood, which is then reintroduced into the animal.

12 Claims, 2 Drawing Sheets

SOLVENT EXTRACTION METHODS FOR DELIPIDATING PLASMA

This application is a 371 of PCT/AU94/00415 filed Jul. 22, 1994 published as WO95/03840 Feb. 9, 1995.

TECHNICAL FIELD

This invention relates to a plasma delipidation system and in particular relates to a method and apparatus for continuously extracting lipids such as cholesterol from blood plasma of animals including humans.

BACKGROUND ART

Safe and effective methods for reducing covers hyperlipidaemia are of great importance in the treatment of coronary heart disease in humans and other animals. Hyperlipidaemia leads to the formation of atherosclerotic plaques with coronary heart disease being an inevitable result.

Diet is the basic element of all therapy for hyperlipidaemia (excessive amount of fat in plasma). However, the use of diet as a primary mode of therapy requires a major effort on the part of physicians, nutritionists, dietitians and other health professionals.

If dietary modification is unsuccessful, drug therapy is an alternative. Several drugs, used singly or in combination, are available. However, there is no direct evidence that any cholesterol-lowering drug can be safely administered over an extended period.

A combination of both drug and diet may be required to reduce the concentration of plasma lipids. Hypolipidaemic drugs are therefore used as a supplement to dietary control.

Many drugs are effective in reducing blood lipids, but none work in all types of hyperlipoproteinemia and they all have undesirable side-effects. There is no conclusive evidence that hypolipidaemic drugs can cause regression of atherosclerosis.

In view of the above, new approaches have been sought to reduce the amount of lipid in the plasma of homozygotes and that of heterozygotes for whom oral drugs are not effective.

Plasmaphersis (plasma exchange) thereapy has been developed and involved replacement of the patient's plasma with donor plasma or more usually a plasma protein fraction. This treatment can result in complications due to the possible introduction of foreign proteins and transmission of infectious diseases. Further, plasma exchange removes all the plasma proteins as well as very low density lipoprotein (VLDL), low density lipoprotein (LDL), and high density lipoprotein (HDL).

It is known that HDL is inversely correlated with the severity of coronary arterial lesions as well as with the likelihood that these will progress. Therefore, removal of HDL is not advantageous.

Known techniques also exist which can totally remove LDL from plasma. These techniques include absorption of LDL to heparinagarose beads (affinity chromatography) or the use of immobilised LDL-antibodies. Other methods presently available for the removal of LDL involve cascade filtration absorption to immobilised dextran sulphate and LDL precipitation at low pH in the presence of heparin. Each method specifically removes LDL but not HDL.

LDL aphaeresis has, however, disadvantages. Significant amounts of other plasma proteins are removed during aphaeresis and to obtain a sustained reduction in LDL-cholesterol. LDL aphaeresis must be performed frequently (up to once weekly). Furthermore, LDL removal may be counter productive: low blood LDL levels will result in increased cellular cholesterol synthesis.

To satisfy the need for a method of achieving a reduction in plasma cholesterol, and in particular LDL-cholesterol, in homozygous familial hypercholesterolemia and heterozygous familial hypercholesterolemia patients other than by diet and/or drug thereapy, an extra corporeal lipid elimination process, termed "cholesterol aphaeresis", has been developed. In cholesterol aphaeresis blood is withdrawn from a subject plasma separated from the blood and mixed with a solvent mixture which extracts lipid from the plasma, after which the delipidated plasma is recombined with the blood cells and returned to the subject.

The advantage of this procedure is that LDL and HDL are not removed from the plasma but only cholesterol, some phospholipids and triglycerides are removed. Our earlier U.S. Pat. No. 4,895,558 describes this system.

While cholesterol aphaeresis has overcome the shortcomings of dietary and/or drug treatments and other aphaeretic techniques, existing apparatus for cholesterol aphaeresis does not provide a sufficiently rapid process. For use in a clinical setting, apparatus is required which effects delipidation in a matter of minutes. Furthermore, flow rates of the order of 70 ml/min are required for cholesterol aphaeresis of a human subject.

SUMMARY OF THE INVENTION

It is an object of the invention to provide a system to allow extraction of cholesterol from animal plasma which may overcome the abovementioned disadvantages.

In one form the invention resides in a method for removing cholesterol from animal plasma comprising subjecting the plasma to a solvent extraction step to extract cholesterol from the plasma, and removing any remaining solvent from the plasma, characterised in that in the solvent extraction step, the plasma is dispersed into small droplets into the solvent by a dispersing means thereby improving the rate of extraction of the cholesterol into the solvent.

The plasma may be human plasma or plasma from other living animals. The plasma can be obtained from human or animal blood by known plasma separating techniques which include centrifugal separation, filtration and the like.

The solvent extraction step is suitably carried out as a continuous or semi-continuous process thereby making the method suitable for continuously extracting cholesterol from plasma. The solvent extraction step may include one or more solvents which can rapidly extract cholesterol from the plasma but do not appreciably extract desirable moieties such as LDL, HDL and VLDL.

Suitable solvents comprise mixtures of hydrocarbons, ethers and alcohols. To allow subsequent removal of any residual solvent from the plasma, it is preferred that the solvent has a relatively low boiling point thereby enabling it to be removed by a combination of heat and possibly vacuum. Preferable solvents are mixtures of lower alcohols with lower ethers. The lower alcohols suitably include those which are not appreciably miscible with the plasma and these can include the butanols (butan-1-ol and (butan-2-ol). C1–4 ethers are also preferred and these can include the propyl ethers (di-isopropyl ether, propyl ether). Other solvents which may be applicable can include amines, esters, hydrocarbons and mixtures providing that the solvent can (1) rapidly and preferably remove cholesterol from the plasma, (2) is substantially immiscible with the plasma, (3) can be quickly removed from the plasma (if required), and (4) does not denature the desired moieties. Preferred solvent compositions are butanol with di-isopropyl ether and these may be in the ratio of 20%–40% of the alcohol with 80%–60% of the ether.

The solvent extraction step may be carried out in a vessel containing the solvent, the vessel being provided with an inlet and an outlet. The inlet through which the plasma may pass can be arranged to be either adjacent the upper or lower parts of the vessel depending principally on the density of the solvent with respect to the plasma. Thus, if the plasma is denser than the solvent, the inlet is preferably adjacent an upper part of the vessel such that the plasma falls through the solvent under the influence of gravity to a lower portion of the vessel. Alternatively, if the plasma is less dense than the solvent, the inlet is preferably adjacent a lower part of the vessel. For the preferred solvent system comprising butanol and di-isopropyl ether, the plasma is denser than the solvent mixture and therefore the inlet is preferably adjacent the upper part of the vessel.

The outlet may also be positioned to collect the plasma after is has been extracted by the solvent. Thus, if the plasma is denser than the solvent, the outlet can be positioned adjacent a lower part of the vessel. Conversely, the outlet may be positioned adjacent an upper part of the vessel should the plasma be less dense than the solvent.

To rapidly allow extraction of the plasma to occur (thereby reducing the time taken to delipidate the plasma), a dispersing means is provided. The dispersing means may be associated with the inlet to disperse the incoming liquid (eg plasma) into fine droplets. The dispersing means may also pass the droplets laterally into the solvent. This provides a distinct advantage over other forms of extraction by ensuring a maximum extraction ability of the solvent. The dispersion means may therefore comprise a spinner which can be rotatably mounted relative to the vessel. The plasma may be introduced into the spinner and then flung laterally out into the solvent by the centrifugal action. Suitably, the spinner also converts the plasma into fine droplets as it rotates.

The solvent extraction step may be used in a continuous manner whereby the plasma can be continuously passed through the inlet, extracted by the solvent and then passed through the outlet. It is found that by using the solvent extraction step as described above, the extraction time can be reduced to between 1 to 5 minutes as opposed to up to 30 minutes for other known techniques.

The delipidated plasma may comprise some entrained solvent which is usually in the form of an emulsion. The delipidated plasma may therefore be treated with a de-emulsifying agent. The de-emulsifying agent may comprise ether and a preferred ether is di-ethyl ether. The delipidated plasma may be passed into a de-emulsifying vessel where it may be contacted with the ether. Again, it is preferred that the delipidated plasma is dispersed with the de-emulsifying agent in order to rapidly de-emulsify the plasma.

The de-emulsified delipidated plasma may be subjected to a further solvent removal step to remove any further solvent (including the de-emulsifying agent) to a acceptable level whereby the plasma can be reintroduced into the human or animal body. Of course, if no remaining solvent is present in the delipidated plasma, or if the level of any remaining solvent is acceptable, a solvent removing step may not be required.

Solvent extraction is a well known procedure whereby a solid or a liquid can have components extracted therefrom into the solvent. With liquid-liquid solvent extraction systems, the solvent and the liquid to be extracted should be substantially immiscible. The solvent should also, or course, be chosen to enable extraction of the desired compound from the liquid. To date, liquid-liquid solvent extraction systems have been conducted manually by shaking the two liquids together in a solvent extraction flask. It is also known to use automatic shakers to effect the same purpose.

A disadvantage with these known systems is that they cannot be used on a continuous basis. This is because the two liquids are vigorously shaken together and the vessel needs to be left standing for a period of time to enable the two liquids to separate. Vigorous shaking is required in order to maximise the solvent extraction step and also to allow the solvent extraction to occur as quickly as possible.

It is of course advantageous to have a solvent extraction step conducted continuously. If this could be achieved, the solvent extraction step could be used in association with other continuous processes which require less handling, manpower and can be fully automated. A fully automated system has several advantages both for clinical uses and also for uses in industrial systems.

The present invention has been developed to provide a solvent extraction apparatus which enables solvent extraction to be carried out on a continuous basis. The apparatus can therefore be used either by itself, or in association with other automated processes. The apparatus enables rapid and efficient solvent extraction to occur without requiring vigorous shaking of the solvent.

In another form, therefore, the invention resides in a solvent extraction apparatus comprising a vessel which can contain a first liquid, an inlet to allow a second liquid to pass into the vessel, an outlet to allow the second liquid to exit from the vessel, and dispersing means associated with the inlet to disperse the second liquid into droplets as it passes into the vessel.

In this manner, the solvent extraction rate can be maximised and the apparatus can be used in a continuous or semi-continuous manner to allow incoming second liquid to be continuously extracted by the first liquid in the vessel.

The position of the inlet in the vessel may depend upon the relative densities between the first and second liquids. If the second liquid is heavier than the first liquid, the inlet is preferably located adjacent an upper part of the vessel. Conversely, if the second liquid is lighter than the first liquid, the inlet is preferably located adjacent a lower part of the vessel.

Similarly, the location of the outlet will also depend upon the relative densities of the liquid. If the second liquid is heavier than the first liquid, the outlet is preferably associated with a lower part of the vessel. Conversely, if the second liquid is lighter than the first liquid, the outlet is preferably associated with an upper part of the vessel. In order to assist separation of the two liquids, the configuration of the vessel in the vicinity of the outlet may be narrowed or tapered relative to the main body of the vessel.

The dispersing means as well as dispersing the second liquid into small droplets, may also function to pass the droplets laterally into the vessel. This can be achieved by having the dispersing means in the form of a spinner. The spinner may be rotatably mounted relative to the vessel. The spinner may comprise a container into which the second liquid can pass. The container may include means to disperse the liquid into droplets. This means may comprise beads (typically glass beads) in the container such that as the container spins about its axis, the beads will disperse the liquid into droplets. The outer wall of the container is suitably perforated such that the dispersed liquid can pass through the wall of the container and laterally into the vessel. Alternatively, the means for dispersing the liquid may comprise a mesh or small apertures in the wall of the container. It is preferred that the container is dimensioned, and is rotated such that second liquid is dispersed laterally substantially through the first liquid in the vessel. Of course, a skilled person will be able to determine the spin rate and size of the container and will also need to take into account the viscosity of the second and the first fluid.

The solvent extraction apparatus can be used for a large range of liquids. These may include plasma and organic solvents, oils, scrubbing liquids and the like.

BEST MODE

Figure 1:
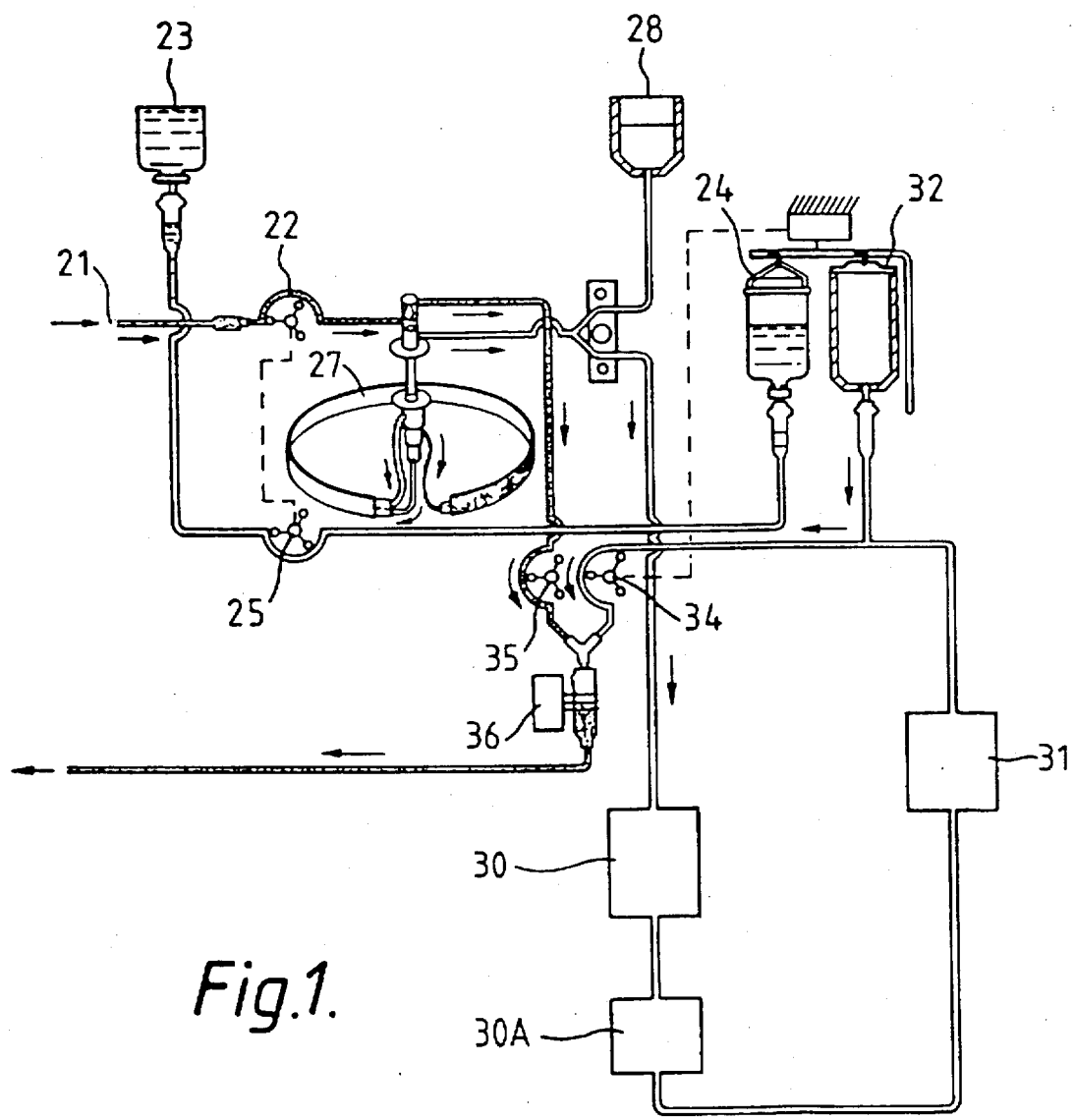
FIG. 1 illustrates a schematic representation of a method for removing cholesterol from plasma.

Referring now to FIG. 1, blood is removed from a subject (not shown) and enters into the system at 21 aided by pump 22. A drawing needle (not shown) is used to extract blood from the subject. Prime solution in reservoir 23 is mixed with the blood and an anti-coagulant from reservoir 24 is also combined with the blood via pump 25. Pumps 22 and 25 are regulated by a venous pressure monitor.

The primed and anti-coagulant treated blood is then fed to a disposable centrifugal separator 27 of known design to separate the plasma (unfilled channel) from blood cells (filled channel). Any waste in the plasma may be diverted to a waste bag 28.

The plasma is passed into a solvent extraction step 30 and is extracted by an apparatus which is more clearly described with reference to FIG. 2. The apparatus 40 includes a vessel 41 having an inlet 42 and an outlet 43. Vessel 41 is filled with solvent which comprises peroxide free di-isopropyl ether and butanol in a 60 and 40 mixture. Inlet 42 comprises a steel tube which is rotatably mounted in a vertical manner by vessel 41. Plasma can pass through the tube through upper end 44 and to the lower end 45. Lower end 45 extends into a dispersing means 46 which is in the form of a cage like mesh container having a horizontal top and bottom wall, and a circular peripheral side wall. Top and bottom walls are formed from continuous material while the circular side wall is formed from perforated material (in the embodiment a mesh). The container is packed with glass balls of approximately 2 millimeter diameter and the mesh is dimensioned to prevent the balls from passing through the side wall of the container. The container can be rotated by a motor (not shown) and is typically rotated at 250 to 350 rpm. It can therefore be seen that as plasma passes through inlet 42 and into the container, the plasma will be forced against the glass balls and thereby will be dispersed into small droplets before being flung out through the mesh side wall into the solvent which fills vessel 41. The container is completely submerged in the solvent and solvent can freely pass into the container.

As the plasma passes into the rotating container, it is dispersed by the beads and flung out through the side wall and into the upper part of the solvent mixture. The fine droplets of plasma will then fall under the influence of gravity towards outlet 43. In the process, a rapid and efficient solvent extraction will take place. This is because the fine droplets continually contact fresh solvent as they pass downwardly through the solvent mixture.

The lower end of vessel 41 is necked to prevent the vortex created by the rotating dispersing means 46 from creating undue turbulence in the lower part of vessel 41.

The delipidated plasma can then pass through outlet 43.

As some solvent is usually retained by the delipidated plasma in the form of a slight emulsion, the delipidated plasma is de-emulsified by passing it into a second vessel 47 (30A in FIG. 1) containing a de-emulsifying agent such as di-ethyl ether. In this vessel, an homogeniser 48 is provided and the delipidated plasma is initially passed into the vessel adjacent the turret 49 of the homogeniser. The action of the homogeniser disperses the delipidated and emulsified plasma into the ether. As the homogenisation takes place in an upper part of the vessel, the de-emulsified and delipidated plasma will drop to a lower part of the vessel 50 where it can separate from the ether and be collected.

Thereafter, as shown in FIG. 1, the delipidated de-emulsified plasma passes to a continuous solvent evaporator 31 where any remaining solvent and ether can be removed or reduced to a level which is no longer harmful to the subject. Replacement fluid solution from reservoir 32 can then be added to the plasma via pump 34 and the plasma is subsequently recombined with the red blood cells via pump 35 and the reconstituted blood can then be returned to the subject via an infusion needle under the control of a level monitor 36.

Figure 2:
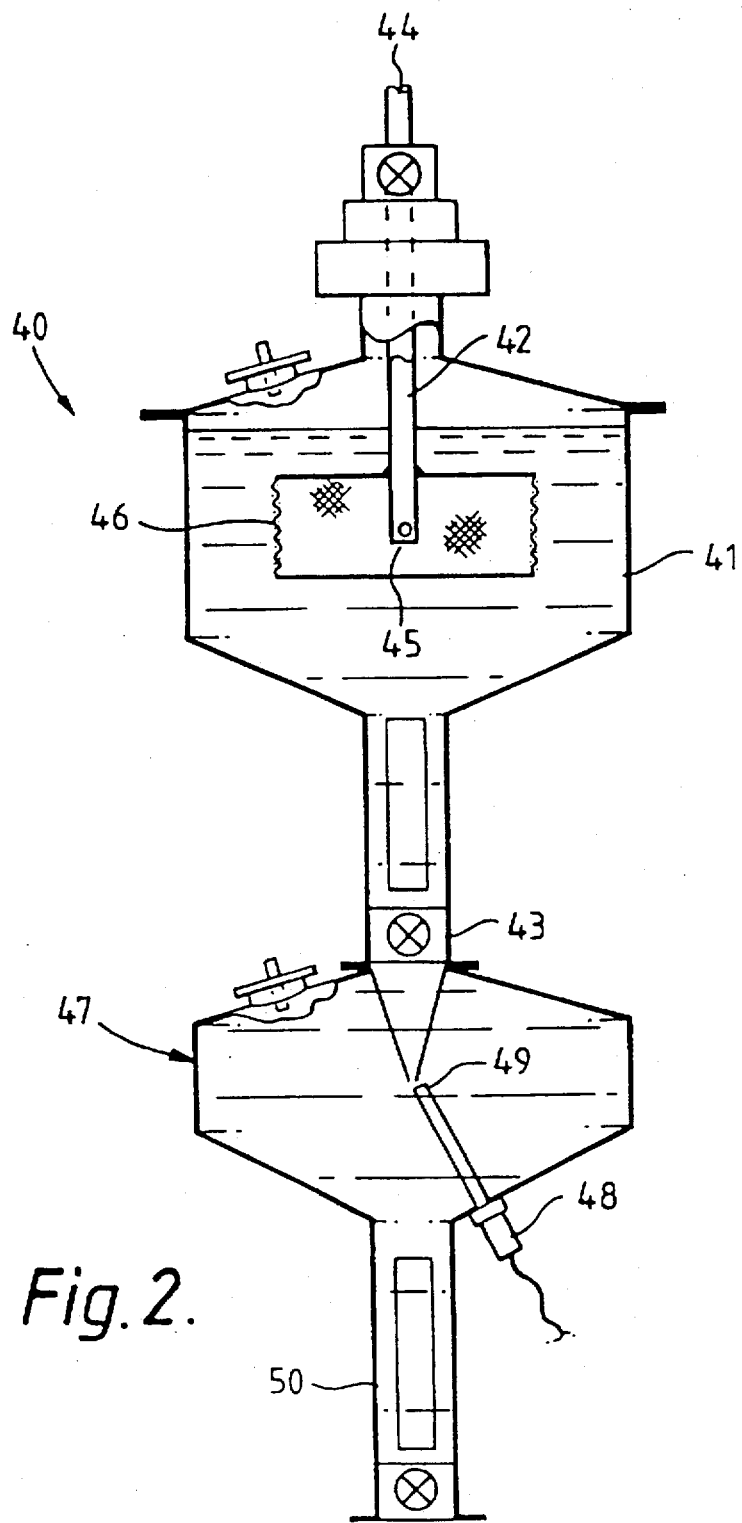
FIG. 2 depicts a solvent extraction apparatus.

The apparatus illustrated in FIG. 2 as well as being used for extracting cholesterol from plasma, can also be used for extraction of any suitable liquid-liquid system and therefore finds use in a wide range of applications.

Referring to FIG. 1, there is illustrated a method for removing cholesterol from plasma and in particular a continuous method for the continuous withdrawal of blood from a subject, extraction of cholesterol from the blood plasma and return of the reconstituted cholesterol depleted blood to the subject.

The system described in FIG. 1 can be used to provide a rapid continuous process in which a plasma volume of about 200 ml can be delipidated in several minutes.

It should be appreciated that various other changes and modifications may be made to the embodiment described without departing from the spirit and scope of the invention as claimed.

I claim:

1. A method for delipidating plasma comprising subjecting the plasma to a solvent extraction step and a de-emulsification step,
    the solvent extraction step being carried out in a first container containing extracting solvent, the first container having a spinning container associated therewith, the solvent extraction step including the steps of passing the plasma into the spinning container, dispersing the plasma into fine droplets by spinning the spinning container, and passing the fine droplets through the extracting solvent to produce delipidated plasma,
    the de-emulsification step being carried out in a second container, the second container having an inlet and a homogenizer and containing a de-emulsifying medium, the de-emulsification step including the steps of passing the delipidated plasma into the second container through the inlet and homogenizing the delipidated plasma and the de-emulsifying medium.

2. The method of claim 1 wherein the homogenizer is adjacent the inlet of the second container.

3. The method of claim 1 wherein the de-emulsifying medium comprises di-ethyl ether.

4. The method of claim 1, wherein the spinning container contains a packing material which assists in dispersing the plasma.

5. The method of claim 4, wherein the packing material comprises a plurality of spheres.

6. The method of claim 5, wherein the plasma is dispersed laterally into the extracting solvent.

7. The method of claim 6, wherein the spinning container is cylindrical and has an outlet comprising a perforated side wall and wherein the step of dispersing the plasma comprises passing the plasma through the side wall and into the extracting solvent.

8. The method of claim 1, wherein the extracting solvent comprises 20–40% of a lower alcohol and 80–60% of a lower ether.

9. The method of claim 8, wherein the lower alcohol comprises butanol and the ether comprises di-isopropyl ether.

10. The method of claim 1, wherein the spinning container comprises an inlet having a lumen in communication with the interior of the spinning container, whereby plasma is supplied to the spinning container through the inlet.

11. The method of claim 1, wherein the extracting solvent comprises a $C_1$–$C_4$ ether and an alcohol which is not appreciably miscible with the plasma.

12. A method for clinically reducing cholesterol in blood of an animal, the method comprising extracting the blood from the animal, subjecting plasma of the blood to solvent extraction to produce delipidated plasma, subjecting the delipidated plasma to a de-emulsification step to produce de-emulsified plasma, recombining the de-emulsified plasma with the removed blood to produce blood having reduced cholesterol, and reintroducing the blood having reduced cholesterol into the animal, the solvent extraction step being carried out in a first container containing extracting solvent, the first container having a spinning container associated therewith, the solvent extraction step including the steps of passing the plasma into the spinning container, dispersing the plasma into fine droplets by spinning the spinning container, and passing the fine droplets through the extracting solvent to produce delipidated plasma, and the de-emulsification step being carried out in a second container, the second container having an inlet and a homogenizer and containing a de-emulsifying medium, the de-emulsification step including the steps of passing the delipidated plasma into the second container through the inlet and homogenizing the delipidated plasma and the de-emulsification step including the steps of passing the delipidated plasma into the second container through the inlet and homogenizing the delipidated plasma and the de-emulsifying medium to produce de-emulsified plasma.

* * * * *